United States Patent [19]

Sambrook et al.

[11] 4,074,569

[45] Feb. 21, 1978

[54] APPARATUS FOR DETERMINING MATERIAL PROCESSING CHARACTERISTICS

[75] Inventors: Ronald William Sambrook; John Harold Beesley, both of Shrewsbury, England

[73] Assignee: Rubber and Plastics Research Association, England

[21] Appl. No.: 755,937

[22] Filed: Dec. 30, 1976

[51] Int. Cl.² ............................................. G01N 3/08
[52] U.S. Cl. .......................................... 73/15.6; 73/94
[58] Field of Search ........................... 73/15.4, 15.6, 94

[56] References Cited

U.S. PATENT DOCUMENTS

| | | | |
|---|---|---|---|
| 2,637,203 | 5/1953 | Gehman | 73/94 |
| 2,691,886 | 10/1954 | Cole | 73/94 |
| 2,754,675 | 7/1956 | More | 73/15.6 |
| 3,550,441 | 12/1970 | Dickinson | 73/94 |
| 3,818,751 | 6/1974 | Karper et al. | 73/15.6 |
| 3,847,018 | 11/1974 | Aston | 73/94 |

Primary Examiner—Herbert Goldstein
Attorney, Agent, or Firm—Diller, Brown, Ramik & Wight

[57] ABSTRACT

An apparatus for testing the processing behavior of a visco-elastic material. A first ram is adapted to apply to a test sample a predetermined pre-test deformation. A second ram is adapted to subsequently apply to the test sample an additional test deformation. The first and second rams are disposed such that their respective piston displacement directions are parallel, whereby both the pre-test and the test deformation are compressive. A control system monitors the load relaxation in the test material.

8 Claims, 3 Drawing Figures

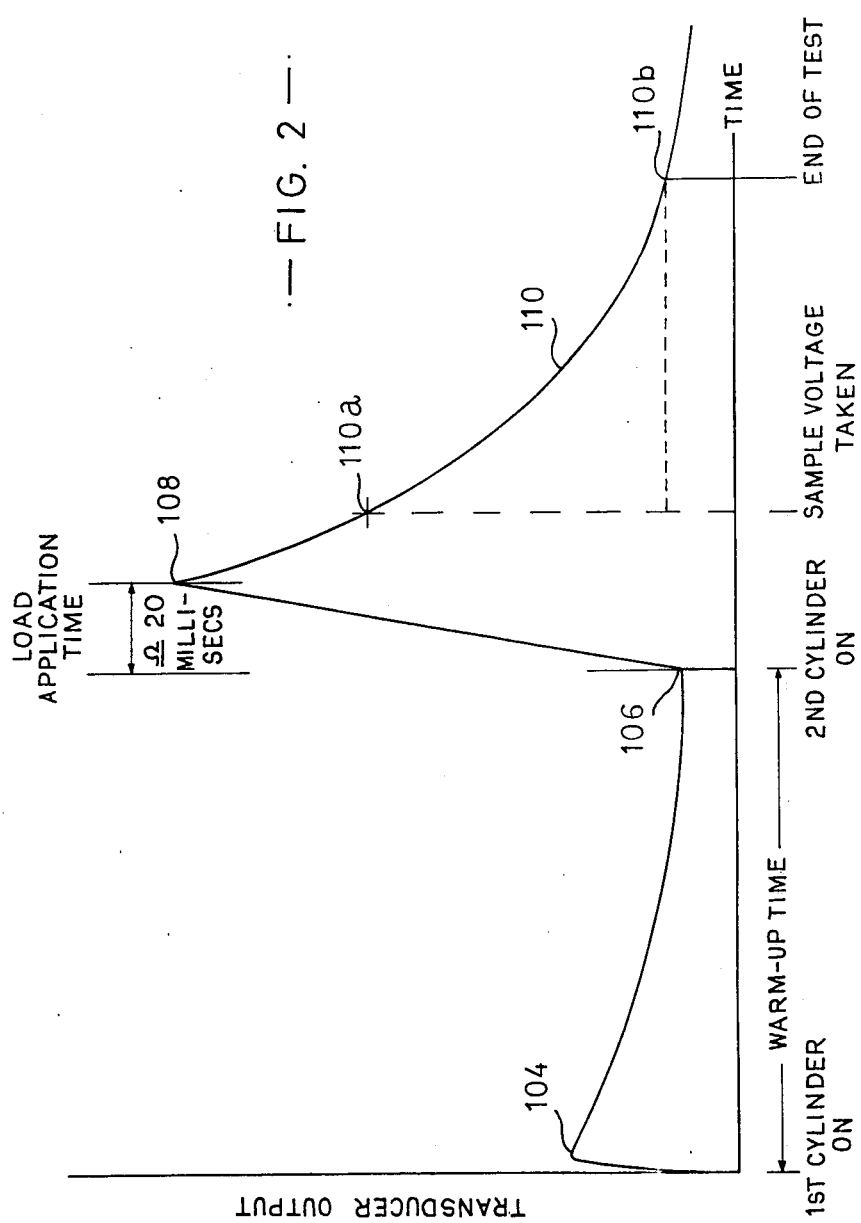

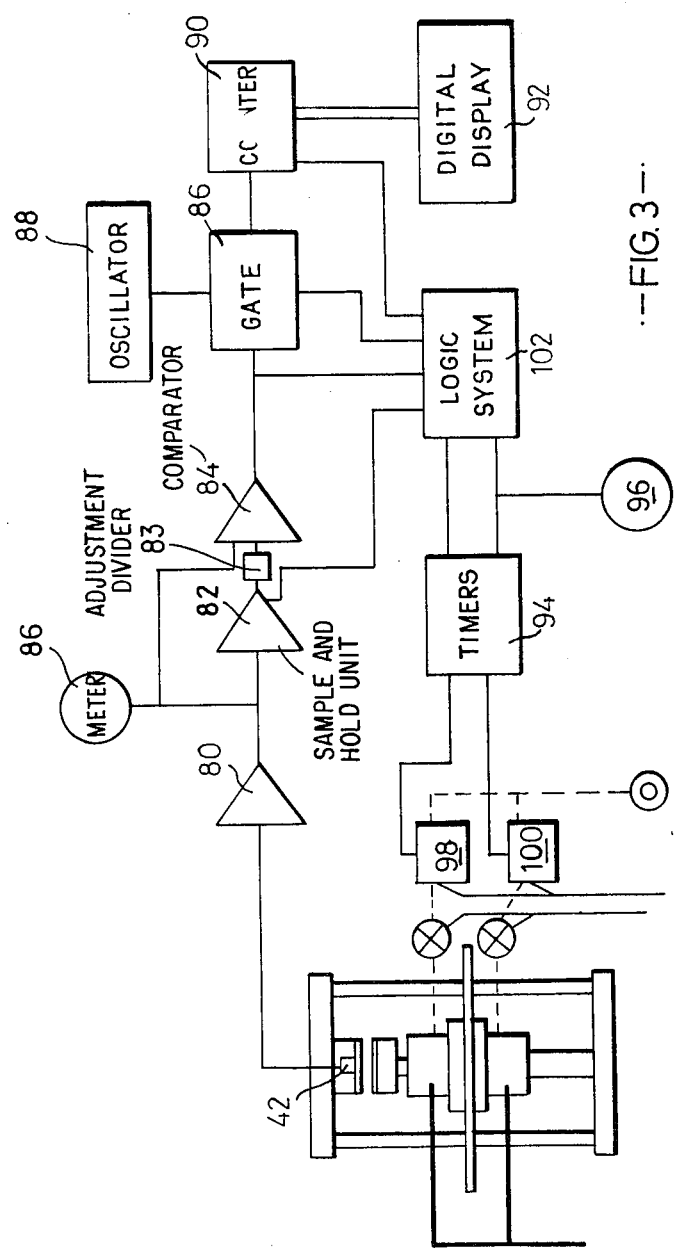

APPARATUS FOR DETERMINING MATERIAL PROCESSING CHARACTERISTICS

The invention relates to an apparatus for testing and characterising material processing behaviour and is particularly concerned with the characterisation of the processing behaviour of uncured elastomeric compounds, such as unvulcanised rubber.

A widespread problem in the rubber industry is the variability in the processing behaviour of nominally identical materials, the variations arising inter alia, from unspecified changes in the microstructure of the raw rubber as well as unscheduled changes in rubber compound mixing procedures. An apparatus is therefore required which will rapidly indicate the processing behaviour of any particular stock of compound to be used in a given process, e.g. in an extrusion process, a calendering or moulding operation or hand assembly.

It is already known that a useful indication of the processing behaviour of elastomeric materials can be obtained by subjecting the material to a predetermined stress and monitoring the time taken for the load in the test material to decay from a peak level to a predetermined ratio or fraction of that level, (U.S. Pat. No. 3,818,751). However, in such known devices it has been the practice to stress the material under test by subjecting it to torsional deformation. This has given rise to the necessity for a relatively complex mechanical arrangement for deriving such torsional deformation and measuring the resulting load in the test sample.

It is an object of the present invention to provide a test apparatus which is mechanically simpler and more robust than the known devices and which is not required to produce torsional loads in the test sample.

In accordance with the present invention, an apparatus for testing the processing behaviour of a visco-elastic material comprises a first ram for applying to a test sample a predetermined pre-compression, a second ram whose piston displacement direction is parallel to that of the first ram, the second ram being for subsequently applying to the test sample an additional test compression, and a control system for monitoring the load relaxation in the test material.

The invention is described further hereinafter, by way of example, with reference to the accompanying drawings, in which:

FIG. 2 is a graph illustrating the timing of the various operative steps occurring during use of the apparatus of FIG. 1, in relation to the output of the pressure transducer; and FIG. 3 is a diagrammatic illustration, partially in block form, of a control and monitoring system for the apparatus of FIG. 1.

Figure 1:
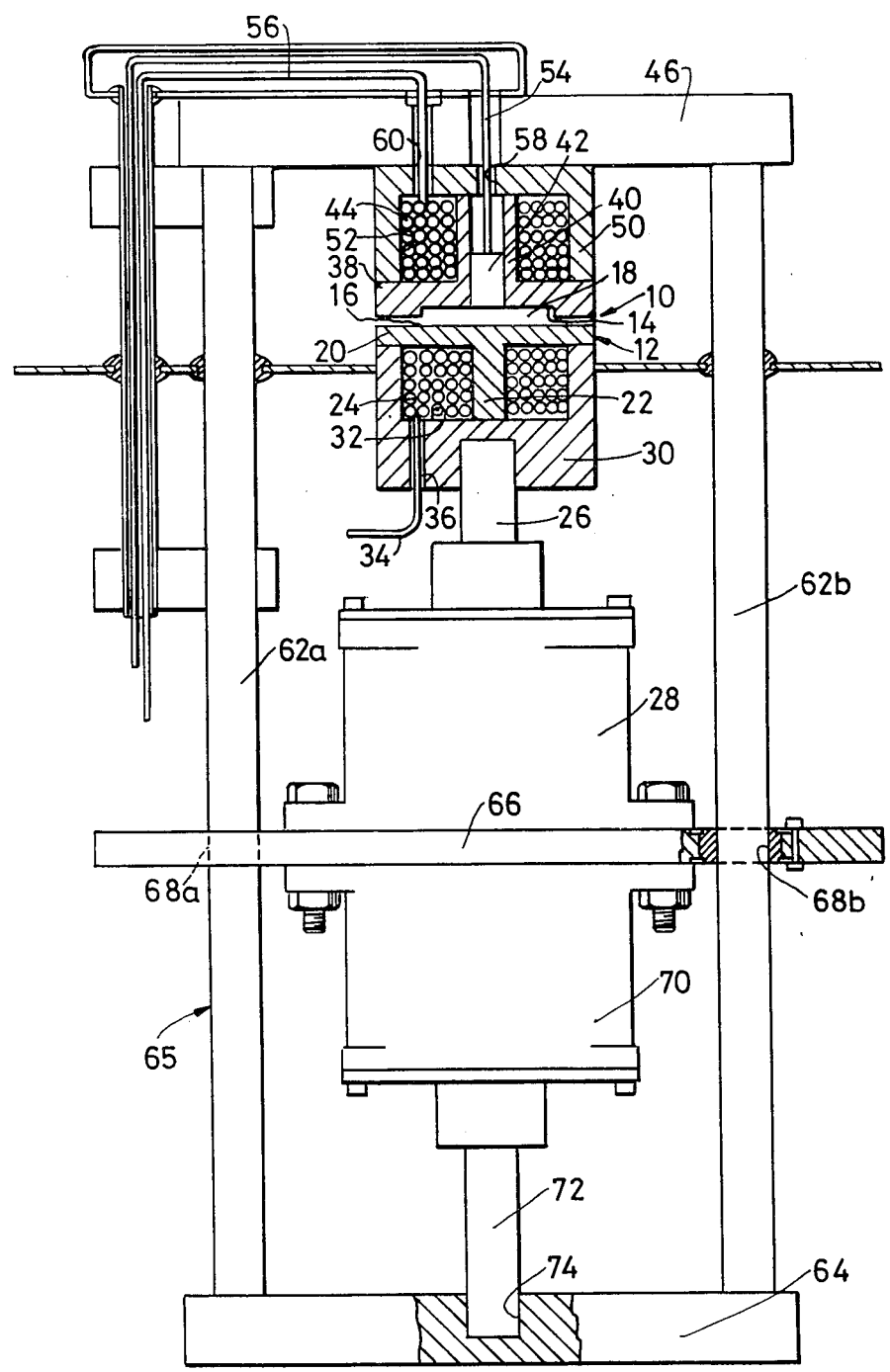
FIG. 1 is a partially sectioned side elevation of one embodiment of an apparatus constructed in accordance with the invention.

The apparatus illustrated in FIG. 1 comprises a pair of relatively displaceable stainless steel members 10, 12, the upper member 10 having a cylindrical recess 14 in its underside which is arranged to co-operate with a flat upper surface 16 of the member 12 to define a compression chamber 18.

The member 12 comprises a plate or platen 20 providing said surface 16 and preferably of circular shape, the plate 20 having a central projection 22 on its underside which is embraced by an electrical heating coil 24 for controlling the temperature of the plate 20 and hence the temperature of the chamber 18. The member 12 is mounted on the free end of the output rod 26 of a pneumatic ram 28 by means of a block 30 of heat insulating material having a cylindrical recess 32 which receives the heating coil 24 and the projection 22. Connecting wires 34 for the heating coil 24 pass through a bore 36 in the base of the block 30.

The member 10 comprises a plate or platen 38 bearing the cylindrical recess 14 and again preferably of circular shape, the plate 38 being formed with a central projection 40 on its upper side having a axial bore which contains a pressure transducer 42 arranged to provide an electrical output signal indicative of the pressure exerted on a test sample when placed in the compression chamber 18. The projection 40 is embraced by a heating coil 44 which is also used to control the temperature of the chamber 18. The member 10 is mounted, co-axially of the member 12, on a cross-head 46 by means of a second block 50 of insulating material having a cylindrical recess 52 which receives the heating coil 44 and the projection 40. Connecting wires 54 for the pressure transducer 42 and connecting wires 56 for the heating coil 44 pass through respective bores 58, 60 in the base of the block 50.

The cross-head 46 is rigidly attached to the one ends of a pair of spaced parallel guide rods 62a, 62b of hard chromium plated steel, the other ends of the guide rods being rigidly connected to a base member 64, whereby the cross-heads 46, base member 64 and guide rods 62a, 62b constitute a generally rectangular frame 65. The ram 28 is mounted on one side of a plate 66 which is arranged to be attached to a fixed foundation when the apparatus is in use, the plate 66 being slidably mounted relative to the rods 62a, 62b by respective bearings 68a, 68b. A further ram 70 is mounted on the other side of the plate 66 such that the two rams 28 and 70 are back-to-back, the output rod 72 of the ram 70 being fixedly received in a recess 74 in the base 64. The arrangement is such that the longitudinal axes of the rams 28 and 70, the member 10 and the member 12 are co-linear, the normal operative orientation of the apparatus being with said co-linear axes extending vertically upwardly from the base 64.

It is also arranged that when the ram 28 is deactuated and the ram 70 is actuated to its full extent, a first predetermined axial spacing exists between the two plates 20 and 38. For example, this spacing might be such that the base of the recess 14 is separated from the surface 16 by a distance of 0.5 cm. Furthermore, by virtue of the engagement of the two plates 20 and 38 on subsequent operation of the other ram 28, there remains a second predetermined axial spacing separating the surfaces between which the sample is being compressed, namely the length of the cylindrical recess 14. This might be for example 0.35 cm.

The test procedure utilising the above described apparatus is as follows. A standard test pellet of a material under investigation is placed centrally on the plate 20 with both rams 28 and 70 deactuated. A controlled current is passed through the two heating coils 24 and 44 for achieving a desired test temperature.

The ram 70 is then actuated to its fullest extent to bring the plates 20 and 38 in the position illustrated in FIG. 1 in which they are separated by said first predetermined axial spacing. The test pellet is thereby subjected to an initial predetermined compression, referred to as the precompression load, which is maintained for a period, e.g. 1 minute, to enable the load (pressure) in the sample to decay to substantially constant value such as zero from the peak which occurs immediately after the precompression is applied.

The ram 28 is then rapidly actuated until the plate 20 engages the plate 38, the second predetermined spacing then prevailing. The sample is thus subjected to an accurately determined, rapid, additional compression, of the order of 30% in the present example with the spacings quoted.

The load in the test sample and the subsequent load decay are monitored by the pressure transducer 42, test results being established and indicated by a control and monitoring system illustrated in block form in FIG. 3.

As indicated in FIG. 3, the output of the pressure transducer 42 is applied, via an amplifier 80, both to a "sample and hold" unit 82 and directly to one input of a comparator 84. The output of the amplifier is monitored by a direct reading meter 86. The other input of the comparator is connected to the output of the "sample and hold" unit 82 via a divider or attenuator 83 which divides or reduces the output of the sample and hold unit by or to a predetermined fraction thereof. The divider or attenuator may be adjustable to enable the predetermined fraction to be varied. The output of the comparator 84 controls a gate 86 to selectively allow pulses from an oscillator 88 to reach a counter 90 whose output may be recorded and/or displayed on a digital display 92.

The system further includes a timing unit 94 connected to a "start" control 96 and adapted to actuate respective solenoid valves 98,100 for the rams 28,70 at predetermined intervals. The timing unit 94, sample and hold unit 82, gate 86 and counter 90 are controlled by a logic unit 102 as follows.

FIG. 2 illustrates the output of the transducer 42 against time during the test procedure described above. The procedure commences with the first ram 70 being actuated to apply the precompression load. The latter rises to a peak at 104 and gradually settles down to a substantially constant value at 106. The second ram 28 is then actuated to apply the main test compression load which rises to a peak at 108, the pressure in the test sample thereafter decaying along a curve 110.

In order to enable the apparatus to provide an output which gives a useful indication of the characteristics of the material under test which will be capable of being compared with previously established test figures to categorize that material, the logic circuit is arranged to determine, from the output of the pressure transducer during the decay portion 110, the time taken for the transducer output to fall from a sampled level to a predetermined ratio or fraction of that level. This is achieved by arranging for the gate 86 to allow pulses from the oscillator 88 to reach the counter 90 starting at a point 110a on the curve 110 and to close the gate 86 to such pulses when the comparator detects that the transducer output has fallen to a second point 110b corresponding to a predetermined ratio of the level at 110a as set by said divider or attenuator (not shown). The digital display 92 thus provides a reading which is directly proportional to the time taken for the level to decay by the predetermined ratio.

The sequence of events from actuation of the switch 96 is as follows. On actuating the switch 96, the first cylinder 70 is energised and an associated timer in the timing unit 94 is started. After a predetermined period determined by the latter timer, the second cylinder 28 is energised and a second timer in the timing unit 94 started. After a second period has elapsed determined by said second timer, the logic system 102 activates the sample and hold unit 82 and opens the gate 86 to initiate counting by the counter 90. By virtue of the aforementioned divider or attenuator (not shown), said other input of the comparator 84 receives a signal corresponding to a predetermined fraction of the value of the sampled output voltage of the transducer 42. The comparator is arranged to provide an output signal when the voltage from the transducer 42 on said one input of the comparator falls to the value of the signal on its other input, i.e. when the transducer output voltage has fallen to the predetermined ratio of the sampled voltage. The occurrence of the comparator output signal is arranged to close the gate 86 to inhibit the count. The output of the counter then provides a value proportional to the time taken for the transducer output to fall from the sampled voltage to the predetermined fraction thereof.

It is intended that the apparatus be normally used for testing samples of elastomer and uncured elastomeric compounds, such as unvulvanised rubber. Uncured elastomeric compounds are visco-elastic materials, that is to say they exhibit properties intermediate between ideally elastic Hookean solids, in which stress is directly proportional to applied strain, independently of time considerations, and purely viscous Newtonian liquids in which stress is directly proportional to applied rate of strain. It is know that variations in processing behaviour are associated with changes in this visco-elastic balance. The manner and rate at which the load in the specimen decays provided by the above-described apparatus provides a sensitive index of the visco-elastic behaviour of the material under test and enables changes in the viscoelastic behaviour from predetermined control levels to be checked and monitored. This is especially useful for determining the consistency of stocks for extrusion.

We claim:

1. Apparatus for testing the processing behaviour of a visco-elastic material, comprising:
   a support;
   a first ram mounted on one side of the support;
   a first platen carried by the piston of the first ram;
   a frame slidably mounted on the support, the frame including elgonate side members slidably received in said support for enabling relative sliding between the frame and support in a direction parallel to the direction of displacement of the piston of said first ram, a first end member disposed on said one side of said support and a second end member disposed on the other side of the support;
   a second platen carried by said first end member of the frame and disposed adjacent said first platen for defining a test chamber therebetween;
   a second ram disposed on the other side of said support between the support and said second end member and with its piston displacement direction parallel to that of said first ram, said first and second rams being displaceable through first and second predetermined distances respectively,
   means for activating said first and second rams in timed sequence,
   and a pressure transducer carried by one of said platens for providing an electrical signal representative of the instantaneous load in a test sample when placed in said test chamber,
   the arrangement being such that actuation of the second ram causes relative displacement of the frame and support to bring the first and second platens into first relative positions wherein they are spaced apart by a first predetermined distance and subsequent actuation of the first ram displaces the first platen relative to the support to bring the first and second platens into second relative positions wherein they are spaced apart by a second, smaller predetermined distance.

2. Apparatus according to claim 1 wherein said first and second rams are mounted back to back on either side respectively of the support.

3. Apparatus according to claim 2 wherein said end members comprise respective cross-heads which extend perpendicularly to the piston displacement direction of said first and second rams.

4. Apparatus according to claim 3 wherein the piston of the second ram is directly connected to said second end member of the frame.

5. Apparatus according to claim 2 including bearing means in said support for slidably receiving said elongate side members of the frame.

6. Apparatus according to claim 1 wherein the support is mounted such that the ram pistons operate in a vertical direction and the first and second platens are horizontal.

7. An apparatus for testing the process behaviour of a visco-elastic material, said apparatus comprising a pair of plates disposed to define a test chamber for receiving a test sample of the material, a first ram means coupled to one of said plates and being displaceable to move said plates towards each other to a position of predetermined first spacing, a second ram means coupled to the other of said plates and displaceable to move said plates towards each other to a position of second predetermined spacing, said first and second ram means having parallel respective piston displacement directions, means for actuating said first and second ram means in times sequence with actuation of said first ram means applying to a test sample a predetermined pre-compression and subsequent actuation of said second ram means applying to the test sample an additional test compression, and pressure responsive means for monitoring the load relaxation in the test material positioned between said plates.

8. An apparatus for testing the processing behaviour of a visco-elastic material, comprising a first ram for applying to a test sample a predetermined pre-compression, a second ram for subsequently applying to the test sample an additional test compression, means for actuating said first and second rams in timed sequence, a support member on which the two rams are mounted back to back with their piston displacement directions parallel, a frame which is mounted such that the support member and frame can effect relative sliding displacement in a direction parallel to said direction of displacement of the ram pistons, a pair of plates between which the test sample is arranged to be compressed during testing, one of said plates being carried by the frame at the side of the support carrying said second ram, the other plate being carried by the piston of said second ram, and the piston of said first ram being connected to the frame at the other side of said support, and a control system for monitoring the load relaxation in the test material.

* * * * *

UNITED STATES PATENT AND TRADEMARK OFFICE
CERTIFICATE OF CORRECTION

PATENT NO. : 4,074,569

DATED : February 21, 1978

INVENTOR(S) : SAMBROOK ET AL

It is certified that error appears in the above–identified patent and that said Letters Patent are hereby corrected as shown below:

ON THE TITLE PAGE, THE ASSIGNEE SHOULD BE AS FOLLOWS:

"RUBBER AND PLASTICS RESEARCH ASSOCIATION OF GREAT BRITAIN"

Signed and Sealed this

Eighth Day of August 1978

[SEAL]

*Attest:*

RUTH C. MASON
*Attesting Officer*

DONALD W. BANNER
*Commissioner of Patents and Trademarks*